(12) United States Patent
Brown et al.

(10) Patent No.: US 12,558,160 B2
(45) Date of Patent: Feb. 24, 2026

(54) SURGICAL LASER FIBER STANDOFF ARRANGEMENT FOR PREVENTING DUST PARTICLE ACCUMULATION DURING A LASER LITHOTRIPSY PROCEDURE

(71) Applicant: OPTICAL INTEGRITY, INC., Panama City Beach, FL (US)

(72) Inventors: Joe D. Brown, Panama City Beach, FL (US); Howard S. Klymas, Panama City Beach, FL (US); Daniel Malphurs, Panama City Beach, FL (US)

(73) Assignee: OPTICAL INTEGRITY, INC., Panama City Beach, FL (US)

( * ) Notice: Subject to any disclaimer, the term of this patent is extended or adjusted under 35 U.S.C. 154(b) by 169 days.

(21) Appl. No.: 18/457,415

(22) Filed: Aug. 29, 2023

(65) Prior Publication Data

US 2024/0164836 A1      May 23, 2024

Related U.S. Application Data

(60) Provisional application No. 63/419,546, filed on Oct. 26, 2022, provisional application No. 63/402,562, filed on Aug. 31, 2022.

(51) Int. Cl.
*A61B 18/26* (2006.01)
*A61B 90/00* (2016.01)
(Continued)

(52) U.S. Cl.
CPC ...... *A61B 18/26* (2013.01); *A61B 2018/2255* (2013.01); *A61B 2090/033* (2016.02); *A61B 2218/005* (2013.01); *A61M 25/0069* (2013.01)

(58) Field of Classification Search
None
See application file for complete search history.

(56) References Cited

U.S. PATENT DOCUMENTS

| | | | | | |
|---|---|---|---|---|---|
| 5,129,896 | A | * | 7/1992 | Hasson | A61B 18/24 606/17 |
| 6,572,609 | B1 | * | 6/2003 | Farr | A61B 18/245 606/17 |

(Continued)

FOREIGN PATENT DOCUMENTS

| | | |
|---|---|---|
| RU | 203570 U1 | 4/2021 |
| WO | WO2017192869 A1 | 11/2017 |

OTHER PUBLICATIONS

Article by Thomas C. Hutchens et al., entitled "Hollow Steel tips for Reducing Distal Fiber Burn-Back During Thulium Fiber Laser Lithotripsy," Journal of Biomedical Optics, 18(7),078001 (Jul. 2013).

*Primary Examiner* — Chris H Chu
(74) *Attorney, Agent, or Firm* — BACON&THOMAS, PLLC

(57) ABSTRACT

An end-firing surgical laser fiber suitable for Thulium Laser Fiber lithotripsy applications includes a standoff that extends beyond the distal end surface of the fiber to prevent contact between the end face of the fiber and a targeted stone. The standoff may either (1) extend along only one side of or partially around a circumference of the fiber, so that dust from the pulverized stone can freely flow downstream from the treatment site without being trapped by or accumulating on the standoff, or (2) include at least one flushing port that prevents dust accumulation by permitting passage of dust from within the standoff. Flushing of dust from within the standoff may be facilitated by including a source of fluid to entrain the dust and carry it through the flushing port.

20 Claims, 3 Drawing Sheets

(51) Int. Cl.
    *A61B 18/22*       (2006.01)
    *A61M 25/00*      (2006.01)

(56)             References Cited

U.S. PATENT DOCUMENTS

| | | | |
|---|---|---|---|
| 7,553,278 B2 * | 6/2009 | Kucklick | A61B 1/00142 |
| | | | 600/114 |
| 11,109,911 B2 | 9/2021 | Brown et al. | |
| 11,172,988 B2 | 11/2021 | Brown | |
| 11,376,071 B2 | 7/2022 | Brown et al. | |
| 11,395,700 B2 | 7/2022 | Brown et al. | |
| 2017/0215965 A1 * | 8/2017 | Harrah | A61B 1/018 |
| 2019/0201100 A1 * | 7/2019 | Brown | A61B 1/0008 |
| 2019/0321104 A1 * | 10/2019 | Brown | A61B 18/24 |
| 2020/0054397 A1 | 2/2020 | Brown | |

* cited by examiner 200 um core 50                    51

50 um core 53              54        55

50 um core 55        52        53

SURGICAL LASER FIBER STANDOFF ARRANGEMENT FOR PREVENTING DUST PARTICLE ACCUMULATION DURING A LASER LITHOTRIPSY PROCEDURE

This application claims the benefit of provisional U.S. Patent Application Ser. No. 63/402,562, filed Aug. 31, 2022, and provisional U.S. Patent Application Ser. No. 63/419, 546, filed Oct. 26, 2022, each of which is incorporated by reference herein.

BACKGROUND OF THE INVENTION

1. Field of the Invention

The present invention relates to a surgical laser fiber having a distal end section to which is fixed a standoff that provides a minimum spacing between the end face of the fiber and a target of the surgical laser.

The surgical laser fiber of the invention may be used with a variety of different laser types, including Thulium Fiber Lasers (TFLs) of the type used in laser lithotripsy (urological stone fragmentation) procedures.

The standoff is configured to prevent accumulation of dust particles that would be trapped within a conventional standoff sleeve. In one embodiment, the conventional standoff sleeve is replaced by a linear, non-cylindrical member that provides spacing but does not have an interior surface within which dust particles and stone fragments can accumulate or become trapped. In another embodiment, the conventional cylindrical standoff sleeve is modified to include a flushing arrangement to remove dust particles and stone fragments from an inside diameter of the sleeve.

The standoff of the present invention may be used with optical fibers having a relatively small core diameter. In order to avoid loss of power density due to the setback provided by the standoff, smaller diameter cores can optionally be tapered outwardly to reduce output beam divergence.

2. Description of Related Art

Laser lithotripsy is a surgical procedure developed during the 1980s to remove impacted stones from the urinary tract, i.e., kidney, ureter, bladder, or urethra, by fragmenting or breaking apart the stones so that they can be more easily excreted by the patient. Early laser lithotripsy used pulsed-dye lasers with picosecond pulse durations to create cavitation bubbles whose collapse caused laser induced shockwaves to fragment the stone. However, the induced shockwave caused a high degree of retro-repulsion, i.e., pushing of the stone way from the laser delivery fiber, and therefore the pulse dye lasers were replaced by pulsed Holmium lasers having longer pulse durations (250 micro seconds) that produced a weaker pressure wave, and therefore less retro-repulsion.

Such laser lithotripsy procedures required frequent replacement of the laser delivery fibers due to fiber degradation. In addition, operators of the Holmium laser frequently encountered sudden flashes that temporarily prevented the operator from viewing the treatment site, forcing stoppage of the laser and prolonging the lithotripsy procedure. It was found that both problems could be traced back to free electron absorption (FEA) by the fiber—as a result of contact between the tip of the fiber and the stone being targeted, and therefore the current inventors proposed to eliminate the possibility of fiber-to-stone contact by providing a standoff sleeve that extended beyond the tip of the fiber to physically maintain a minimum spacing between the fiber and the stone. As described in the inventor's PCT Appl. Ser. No. PCT/US2017/031091 (PCT Publ. No. WO/2017/192869), filed May 4, 2017, the spacer tip or standoff sleeve consisted of a cylindrical structure placed over a stripped end of the fiber, and arranged to extend a predetermined distance beyond the end to act as a physical barrier between the fiber and a stone. Not only did the standoff sleeve prevent contact between the fiber and the stone but, by making the sleeve out of a relatively soft material such as PTFE or ETFE, the standoff sleeve could be used to protect the inner surface of an endoscope during insertion of the fiber through the scope to the treatment site.

Further enhancements to the PTFE or ETFE spacer tips or standoff sleeves, and/or methods of utilizing the cylindrical spacer tips or sleeves during laser lithotripsy procedures, included the arrangements and methods disclosed by the inventors in U.S. patent application Ser. No. 15/992,609, filed May 30, 2018 (now U.S. Pat. No. 11,109,911); U.S. patent application Ser. No. 16/353,225, filed Mar. 14, 2019 (now U.S. Pat. No. 11,376,071); Ser. No. 16/414,255, filed May 16, 2019 (now U.S. Pat. No. 11,395,700); U.S. patent application Ser. No. 16/234,690, filed Dec. 28, 2018 (U.S. Patent Publication No. 2019/0201100); and U.S. patent application Ser. No. 16/546,992, filed Aug. 21, 2019 (U.S. Patent Publication No. 2020/0054397). For example, the inventors discovered that by appropriately controlling the laser, or by use of an additional continuous wave laser, liquid in the interior passage between the end of the fiber and the end of the sleeve could be vaporized, resulting in formation of a liquid-free passage from the tip of the laser fiber to the stone (known as the "Moses" effect) and consequently reduced power requirements, enhanced stone fragmentation efficiency, and shortened treatment times.

However, while the above-described PTFE or ETFE spacer tips or standoff sleeves were well-suited for use with existing pulsed Holmium:YAG laser systems, problems arise when used with continuous wave/high frequency Thulium fiber lasers (TFLs). TFLs have recently replaced pulsed Holmium:YAG lasers for many lithotripsy applications because of their relatively small Gaussian beam profile, which allows use of smaller fiber core diameters (improving fiber flexibility and irrigation in the single working channel of the scope, increasing visibility, and reducing stone retro-repulsion), and because the lack of pulse intervals prevents fragments of stone from breaking away and escaping the path of the laser during the intervals. On the other hand, the smaller cross-section and higher power density of a TFL fiber leaves the fiber more vulnerable to degradation due to free electron absorption and increased temperatures at the treatment site. Thulium fiber lasers typically have an output frequency of 5-2500 Hz, as compared to 5-100 Hz for a pulsed Holmium laser, resulting in substantially increased heat generation at the treatment site, which can destroy spacer tips or standoff sleeves of the type described above, leaving no way to prevent fiber-to-stone contact.

One solution to reducing FEA-induced fiber degradation caused by higher temperatures at the treatment site is simply to increase the size of the fiber, resulting in a more robust fiber that is able to withstand higher temperatures and to absorb reflected radiation, but this would negate the advantages of increased flexibility and enhanced irrigation resulting from the smaller fiber diameter made possible by the use of continuous wave Thulium fiber lasers. In order to maintain the advantages of a thinner fiber while at the same time reducing fiber degradation by providing a more robust fiber exit surface, it has been proposed to provide an outward taper at the end of the fiber, as disclosed for example in U.S. patent application Ser. No. 15/417,934, filed Jan. 27, 2017 (now U.S. Pat. No. 11,172,988). However, as discussed in Section 1.3 on page 2 of the article by Thomas C. Hutchens et al. entitled "Hollow Steel tips for Reducing Distal Fiber Burn-Back During Thulium Fiber Laser Lithotripsy," *Journal of Biomedical Optics*, 18(7), 078001 (July 2013), the tapered fiber is still vulnerable to damage and burn-back, and furthermore more delicate and subject to fracture during handling. To protect the fiber, the Hutchens article proposed to replace the tapered fiber tip with a hollow steel tube glued to, and arranged to surround and extend beyond, the end of a conventional non-tapered, cylindrical fiber.

More generally, it has been proposed in provisional U.S. Patent Application Ser. Nos. 63/324,676, filed Mar. 29, 2022, and U.S. Patent Application Ser. No. 63/247,427, filed Sep. 23, 2021, to replace PTFE or ETFE spacer tips or standoff sleeves in high temperature TFL lithotripsy applications with standoff sleeves made of a highly reflective ceramic, glass, or metal material that is welded to the fiber, or sleeves with a heat resistant coating.

A problem with the heat resistant spacer tips or standoff sleeves disclosed in provisional U.S. Patent Appl. Ser. Nos. 63/324,676 and 63/247,427 is that the tips or sleeves are vulnerable to FEA caused by accumulation of dust particles on the inside diameters of the cylindrical sleeve structures. The dust particle problem is addressed by modifying the laser output to include low power long-duration single or multiple pulses that serve to flush suspended dust particles from the inside of the standoff sleeve. The particle-flushing pulses could be applied periodically, as a pre-pulse, or in response to detection of excess radiation or FEA, for example by using the stone-sensing method described in U.S. patent application Ser. No. 15/992,609, filed May 30, 2018 (now U.S. Pat. No. 11,109,911), and U.S. patent application Ser. No. 17/400,380, filed Aug. 12, 2021.

While the use of particle-flushing pulses has shown promise in preventing FEA resulting from buildup of dust particles on the inside of the standoff sleeve, flushing solely by adding pulses to the laser output may not be adequate for all lithotripsy applications, and especially applications that utilize higher power Thulium lasers. Although higher power lasers have the advantage of more completely pulverizing stone fragments, avoiding the creation of larger fragments that can become trapped downstream of the treatment site, the increase stone pulverization efficiency can aggravate the dust accumulation problem, due to the creation of additional suspended dust particles. If too many dust particles build up inside the sleeve, the temperature of the fiber tip can still exceed 1000° C. and create FEA similar to the FEA that occurs when a fiber tip contacts a stone in the absence of a sleeve, resulting in rapid fiber degradation. As a result, the inventors have found that advances in stone pulverization efficiency has actually increased the need for a way to prevent dust accumulation in laser surgery systems that utilize standoff sleeves or protective tips.

One possible approach to the problem of increased dust accumulation resulting from more efficient stone pulverization is to use suction to remove stone fragments and particles, as disclosed in U.S. Patent Publication No. 2017/0215965. However, this arrangement is not applicable to laser systems that use a standoff sleeve at the tip of the fiber. Instead, in a system of the type disclosed in U.S. Patent Publication No. 2017/0215965, it is necessary to supply the irrigation fluid through multiple side ports in the introducer, so as to leave open the distal end of the introducer and allow suction to be applied though the distal end of the introducer, causing dust particles to be pulled into the introducer for removal while also preventing retro-repulsion of the target stone. Because the laser fiber extends from the end of the introducer and no standoff is provided, the use of suction for dust removal and to draw the stone towards the laser fiber, as described in U.S. Patent Publication No. 2017/0215965, has the disadvantage of increasing the chance of contact between the laser fiber and the targeted stone—a disadvantage that the use of standoff sleeves seeks to prevent.

Consequently, suction systems cannot be used to remove dust in systems requiring a standoff or protective sleeve, despite the potentially serious consequences presented by dust accumulation in the sleeve. Current standoff sleeve systems do not provide any way to prevent such accumulation and no such dust removal arrangements have been proposed, other than the use of low power, long-duration single or multiple pulse arrangements disclosed in the above-discussed provisional U.S. Patent Application Ser. Nos. 63/324,676 and 63/247,427.

The current lack of appreciation for the problem of dust accumulation is evidenced by the fact that some proposed arrangements actually seek to trap, rather than remove, the particles or fragments resulting from stone pulverization, increasing rather than reducing dust accumulation. One such particle trapping arrangement is disclosed in Russian Patent Publication 203570U1, entitled "Endoscopic Probe Tip for Contact Laser Lithotripsy," which discloses a cylindrical sleeve for the end of a laser lithotripsy fiber that includes two nozzles for (a) reducing fluid pressure due to shockwaves (the hammer effect), and (b) intentionally trapping flying stone fragments within the cylinder. The reason for intentionally trapping stone fragments is to prevent them from causing damage or becoming lodged in the urinary tract downstream of the treatment site, but this has the unintended effect of also trapping dust that can accumulate and cause fiber degradation resulting from FEA, since there is no provision for flushing the particles or preventing them from becoming trapped within the standoff cylinder together with larger stone fragments. In order to remove the fragments and dust during a lithotripsy procedure, the operator must interrupt the procedure, withdraw the fiber, and manually remove the fragments and dust, prolonging treatment time.

The present invention takes a contrary approach to the residue from a pulverized stone, addressing the problem of dust accumulation in a standoff or protective sleeve, by either configuring the standoff to eliminate interior, dust trapping spaces, or by adding a flushing arrangement that utilizes at least one flushing port through which suspended dust particles from the inside of a standoff or protective sleeve are removed from the inside of the sleeve.

SUMMARY OF THE INVENTION

It is accordingly an objective of the present invention to provide an improved optical fiber arrangement for laser surgery applications.

It is a second objective of the present invention to provide a standoff for providing a minimum spacing between the tip of an optical fiber and a stone during laser lithotripsy applications, which is suitable for use with high power Thulium fiber lasers, and which does not trap or allow build-up of dust particles.

It is a third objective of the invention to provide an optical fiber arrangement for laser surgery applications, in which fiber life is extended by not only eliminating the possibility of unintentional contact between the fiber tip and the stone through the provision of a "standoff," but also by preventing dust build-up or accumulation within the standoff, which can also lead to FEA-induced fiber degradation.

It is a fourth objective of the invention to provide a standoff sleeve for the purpose of maintaining spacing between laser lithotripsy fiber tip and a stone, and which further includes a flushing arrangement for preventing build-up of dust particles on the inside of the sleeve.

It is a fifth objective of the invention to provide a method of preventing damage caused by dust particle buildup on the inside diameter of a standoff sleeve, by modifying the standoff sleeve to include at least one debris flushing port, and a source of pressurized fluid to flush suspended dust particles from the interior of the standoff sleeve.

These and other objectives of the invention are achieved, in accordance with the principles of an exemplary embodiment of the invention, by modifying a standoff of the type described, for example, in copending provisional U.S. Patent Application Ser. No. 63/324,676, filed Mar. 29, 2022, and U.S. Patent Application Ser. No. 63/247,427, filed Sep. 23, 2021, each of which is hereby incorporated by reference, to positively prevent dust accumulation on surfaces of the standoff.

Prevention of dust accumulation within the standoff is achieved by modifying the conventional cylindrical standoff sleeve to (1) extend on one side of or only partially around a circumference of the fiber, so that particles are not trapped within the interior of the sleeve, (2) surround the end of the fiber but include at least one port through which dust-particle containing fluids are flushed from the interior of the sleeve, and (3) include at least one port and a source of fluids that entrain and flush particles through the at least one port. The fluids can be gaseous or liquid.

In exemplary embodiments of the invention, the standoff may be made, by way of example and not limitation, of metal, a glass material such as silica glass, or sapphire, a ceramic, a polymer, or a material with a heat-resistant coating. In addition or alternatively, the inner diameter of the sleeve may be provided with coatings protect the material of the sleeve from excessive heat by enhancing reflectivity.

By way of example and not limitation, the standoff of the preferred embodiments may be fixed to the outer diameter of an end section of the fiber by welding. Welding of the standoff to the fiber provides the further advantage of providing a heat conductive connection that enable the sleeve to serve as a heat sink, although it is also within the scope of the invention to utilize other adhesive or mechanical methods (such as crimping) to fix the reflective standoff sleeve to the fiber, depending on the material of the reflective standoff sleeve.

The standoffs of the exemplary embodiments of the present invention may be used with surgical laser fibers having a reduced core diameter and therefore advantages of increased fiber flexibility, better irrigation flow, improved visibility, and lower retro-repulsion. Effects on output beam power density may be mitigated by outwardly tapering the fiber core, which reduces beam dispersion and thereby allows a greater setback between the tip of the fiber and the distal end of the standoff sleeve, which decreases FEA.

A suitable outwardly tapered fiber arrangement is disclosed, for example, in the above-cited copending U.S. Provisional Patent Application Ser. Nos. 63/324,676 and 63/247,427. In addition, a modified implementation of the outward taper arrangement disclosed in the copending applications, for a fiber with a core dimeter of 25 µm, is described in detailed herein. However, although the use of outwardly tapered fibers has the advantage of enabling enhanced fiber flexibility, better irrigation flow, and so forth, the standoffs of the present embodiments are not limited to use with tapered fiber configurations, but rather may be used with a variety of different fiber types, setbacks, and so forth, depending on the requirements of specific applications, as described below.

In addition to preventing dust accumulation, the standoffs of exemplary embodiments of the invention may offer the advantage of providing a platform for precisely positioning sensors or detectors at the treatment site. Conventionally, sensors or detectors have been positioned in the introducer or on a sleeve surrounding the fiber. However, since the fiber must be extended from the introducer, the position of the sensor or detector relative to the end of the fiber is either variable, or the sensor or detector is vulnerable to degradation of the fiber and/or sleeve on which the sensor or detector is positioned. The use of a standoff that extends from the end of the fiber allows the sensor or detector to be precisely positioned relative to the end of the fiber while providing a secure mounting platform that is not resistant to degradation.

BRIEF DESCRIPTION OF THE DRAWINGS

FIG. 6B illustrates an optional arrangement for reducing output beam divergence of a smaller core diameter fiber.

DETAILED DESCRIPTION OF THE PREFERRED EMBODIMENTS

Figure 1:
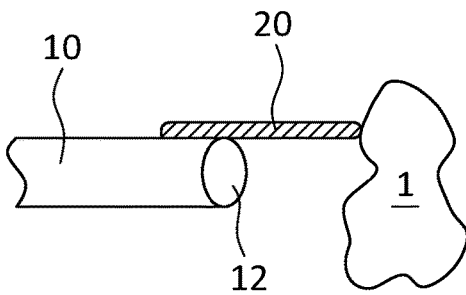
FIG. 1 is a cross-sectional side view of a laser lithotripsy standoff arrangement constructed in accordance with the principles of a first exemplary embodiment of the present invention.

As shown in FIG. 1, a laser lithotripsy fiber tip arrangement constructed in accordance with principles of a first preferred embodiment of the invention includes a laser lithotripsy optical fiber 10 arranged to transmit laser energy to a stone 1 from a laser that has been coupled to a proximal end of the fiber (not shown). As is conventional, the optical fiber 10 is inserted through a scope (not shown) until the distal end 12 of the fiber, as viewed through the scope, faces a stone 1 that has obstructed the urinary tract of the patient and needs to be destroyed. In the embodiment shown in FIG. 1, the distal end 12 of the fiber includes a planar end face, through which laser energy exits the fiber 10 and is directed at the stone 1 visible through the scope, to break the stone apart.

To maintain spacing between the stone 1 and the distal end 12 of the optical fiber 10 of this embodiment, a first end of a standoff 20 is welded or otherwise fixed to the fiber at one or more locations adjacent the distal end 12 of the fiber

10, so that the opposite end of the standoff 20 extends a predetermined distance beyond the end face of the fiber. The standoff 20 may be made of any material capable of withstanding high temperatures at the treatment site, and is elongated in an axial direction of the fiber to positively prevent the stone 1 from coming into contact with the fiber end face. However, unlike conventional standoff sleeves for lithotripsy application, the standoff 20 of this embodiment extends only partially around a circumference of the optical fiber 10, so that at least one gap in the standoff is formed to prevent dust particles from being trapped in the fiber.

The standoff 20 of this embodiment may extend along only one side of the fiber, on multiple sides of the fiber, or substantially around the circumference, leaving one or more slots or gaps through which dust can exit the standoff 20. The standoff 20 of this embodiment may have a cross-section of any desired shape, including circular or rectangular, and may include a single or multiple elongated members, each fixed to the fiber. As with the conventional cylindrical standoff tip of sleeve, the length of the standoff 20 is determined by the desired minimum spacing between the fiber end 12 and the stone 1.

Because the standoff 20 of this embodiment does not have the particle-trapping inner passage of a conventional cylindrical sleeve, the standoff does not trap larger particles, which can potentially still become lodged in the urinary tract of the patient, downstream from the treatment site. As a result, this embodiment is especially suitable for use with high frequency Thulium Fiber Lasers (up to 2 KHz), which produce smaller stone fragments that do not need to be captured because they are small enough to pass through the urinary tract without causing a blockage.

Optionally, the standoff 20 may also provide a stable platform for mounting a sensor or detector 22, such as a temperature sensor, at a predetermined position relative to the fiber end 12. Although depicted in connection with the embodiment of FIG. 1, it will be appreciated that the addition of a temperature sensor or other sensor or detector is not limited to the illustrated standoff, and that any of the embodiments disclosed herein may support a sensor or detector.

Figure 2:
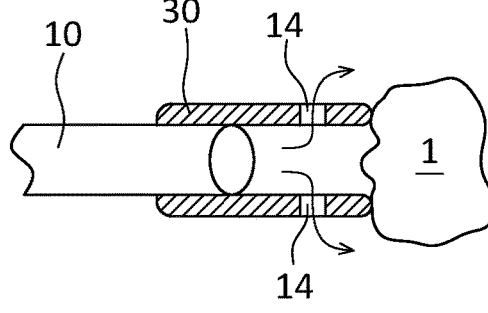
FIG. 2 is a cross-sectional side view of a laser lithotripsy standoff arrangement constructed in accordance with the principles of a second exemplary embodiment of the invention.

The second exemplary embodiment shown in FIG. 2 uses a standoff 30 that is similar to the conventional standoff sleeve in that it surrounds the end of the fiber and includes a central bore through which the laser is fired from distal end 12 towards the stone 1. For example, this sleeve may be similar to the ones described, by way of example, in provisional U.S. Patent Application Ser. Nos. 63/324,676 and 63/247,427. However, unlike the conventional standoff sleeves the standoff sleeve of this embodiment of the invention is modified to include at least one port 14, and preferably multiple ports, through which dust particles may escape the sleeve, thereby preventing dust accumulation within the sleeve.

Expulsion of the dust particles through the ports 14 of this embodiment may be facilitated by the shockwaves induced by laser pulses during surgery, for example by controlling the laser to add low power, long duration single or multiple pulses that cause retro repulsion of the suspended dust particles to clear them from the interior of the sleeve, as described for example in provisional U.S. Patent Application Ser. Nos. 63/324,676 and 63/247,427, but the additional pulses are optional. The low frequency, low power pulses may simply be added to a high frequency pulse train at regular intervals, or inserted into the laser output whenever a detector senses the presence of excessive radiation caused by dust particle buildup or FEA. Alternatively, clearing of suspended dust particles can also be achieved by use of a single continuous background pulse or waveform, or by adding a pre-pulse for each or initiated therapeutic pulse. The dust particle clearing pulses can be created by modulation or appropriate control of the main therapeutic laser, or by a secondary laser.

It will be appreciated by those skilled in the art that although this embodiment may be used for TFL applications, with appropriate selection of standoff sleeve materials, it may also be used with lower frequency Holmium lasers (100 Hz or less) that have high peak powers (15 kWatts). If Thulium lasers are used, silica or quartz is preferred as material for the sleeve, because of its higher heat resistance and/or heat sink properties. If Holmium lasers are used, then the tubing material may be varied to include softer materials with lower heat resistance.

Figure 3:
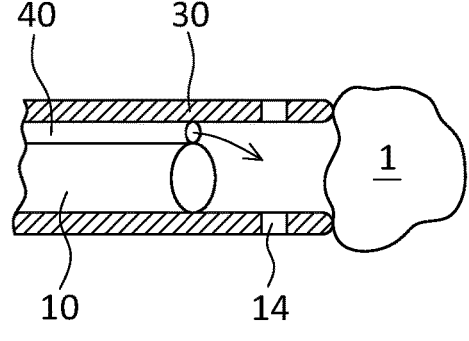
FIG. 3 is a cross-sectional side view of a laser lithotripsy standoff arrangement constructed in accordance with the principles of a second exemplary embodiment of the invention.

In the embodiment illustrated in FIG. 3, a source 40 of fluid that is added to facilitate flushing of particles through the ports 14, in place of or in addition to the use of dust expulsion methods that involve the addition of retro-repulsion inducing background pulses or waveforms. The fluid source 40 may be a hose through which a gas or irrigation liquid is supplied. The distal end of the fluid source 40 may be positioned near or behind the distal end 12 of the fiber to ensure that all particles in the space between the fiber end 12 are entrained in the fluid flow and flushed out through the ports 14.

In the embodiments of FIGS. 2 and 3, the size or diameter of the ports 14 may be selected to permit dust particles to pass, while preventing passage of larger particles. Larger particles that remain in the central bore 31 of the sleeve (see FIG. 5) will still be exposed to the main laser, and therefore continue to be fragmented until the fragments are reduced to dust sized particles that can be flushed through the ports 14.

Figure 4:
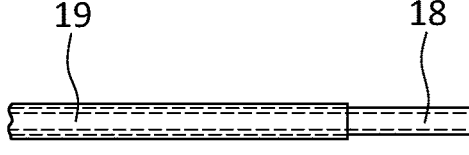
FIG. 4 is a side view showing additional details of the standoff arrangement shown in FIG. 2.

FIG. 4 shows additional details of the sleeve or ferrule 30 shown in FIGS. 2 and 3. As shown in FIG. 4, the sleeve or ferrule 30 of this embodiment may be in the form of a silica tube that is welded to the silica cladding 17 of the fiber. The silica cladding 17 is exposed by removal of polymer cladding 18 and ETFE buffer 19. Alternatively, the standoff sleeve may be made, by way of example and not limitation, of metal, a glass material such as silica glass, or sapphire, a ceramic, a polymer, or a material with a heat-resistant coating, while the inner diameter of the sleeve may be provided with coatings protect the material of the sleeve from excessive heat by enhancing reflectivity.

Figure 5:
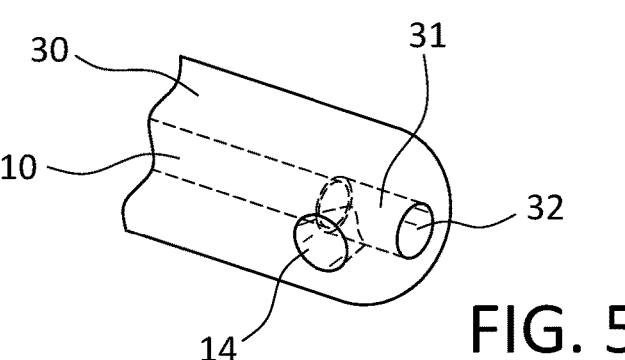
FIG. 5 is an isometric view of the standoff arrangement of FIGS. 2 and 4.

As shown in FIG. 5, the two ports 14 may be constructed as branches of the central bore 31 that extends within sleeve 30 from the tip of the fiber 10 to an opening 32 through which laser energy from the fiber exits the standoff sleeve to impact the stone 1. Although depicted as cylindrical, it will be appreciated by those skilled in the art that the central bore 31 and ports 14 may have shapes other than cylindrical, as may the standoff sleeve itself.

Although not shown, it is within the scope of the invention to include an optional filler material or reinforcing structure, the filler material or reinforcing structure preferably being index matched to the material of the sleeve so that the index of refraction is equal to or higher than that of the cladding, to absorb, transmit, or scatter energy that might otherwise back-propagate through the fiber towards the scope.

Figure 6A:
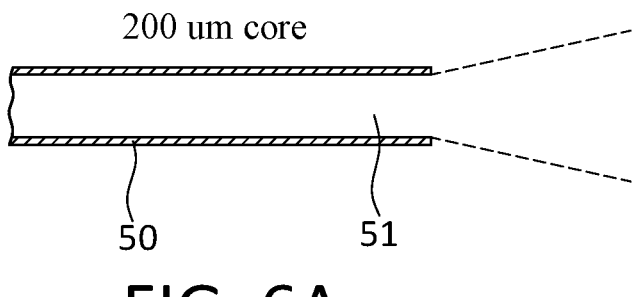
FIGS. 6A-6C illustrate the effect of optical fiber core diameter on laser output beam divergence, and therefore power density.
Figure 6B:
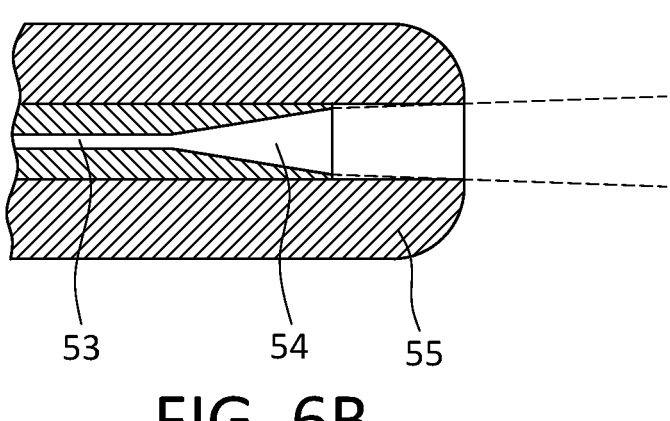

The standoffs of the exemplary embodiments of the invention may be used surgical laser fibers having a smaller diameter. To mitigate the effect of increased output beam divergence resulting from the smaller core diameter, which can be understood from a comparison between the output of the fiber 50 shown in FIG. 6A, which has a 200 μm core 51, and the fiber 52 shown in FIG. 6C, which has a 50 μm core 53, the distal end of the 50 μm core fiber may be modified as shown in FIG. 6B to have an outward taper 54, for example of the type disclosed in U.S. Provisional Patent Application Ser. Nos. 63/247,427 and 63/324,676. The outward taper decreases beam divergence, and thereby allows an increased setback within the standoff 55 to further minimize FEA without significant loss in power density. Optionally, the entire assembly shown in FIG. 6B may be fused to increase strength and provide a heat sink, while a filter may be provided behind the taper to remove any remaining FEA from the fiber. Still further, the illustrated embodiments of the invention may be used with a system that detects FEA propagation through the cladding back towards the proximal end of the fiber, and interrupts the laser if significant detection of FEA is detected. In this regard, the thicker cladding of smaller core diameter fibers can help lower the density of FEA in the cladding, reducing the need to interrupt the laser and prolong a treatment procedure.

Figure 6C:
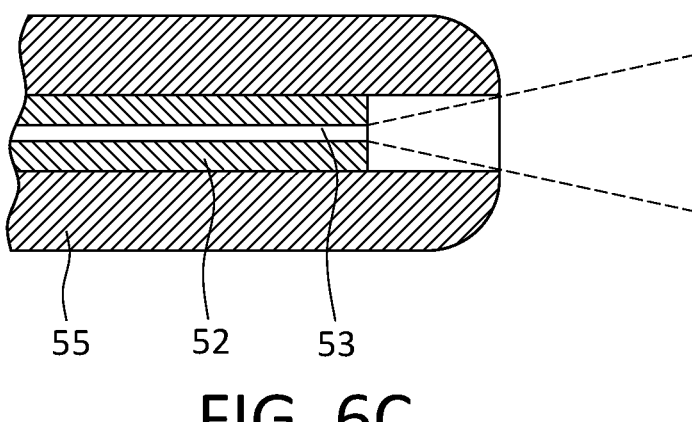

Although the exemplary embodiments shown in FIGS. 6B and 6C have a number of advantages, including increase fiber flexibility and irrigation flow as noted above, it is intended that the present invention not be limited to a particular fiber core diameter. The standoffs of the illustrated embodiments may be used with 200 μm core diameter fibers as well as 50 μm or smaller core diameter fibers, and with non-tapered as well as outwardly-tapered fibers.

Figure 7A:
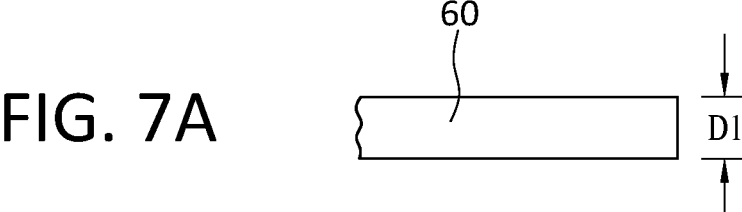
FIGS. 7A-7D illustrate a specific implementation of the tapered fiber arrangement shown in FIG. 6B.
Figure 7B:
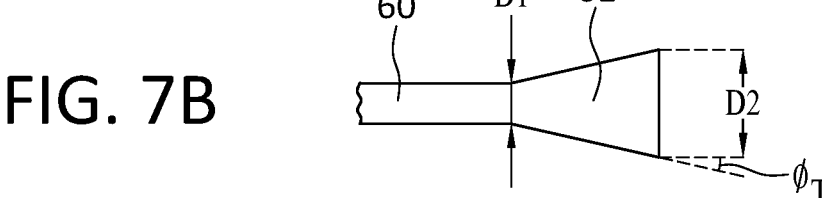
Figure 7C:
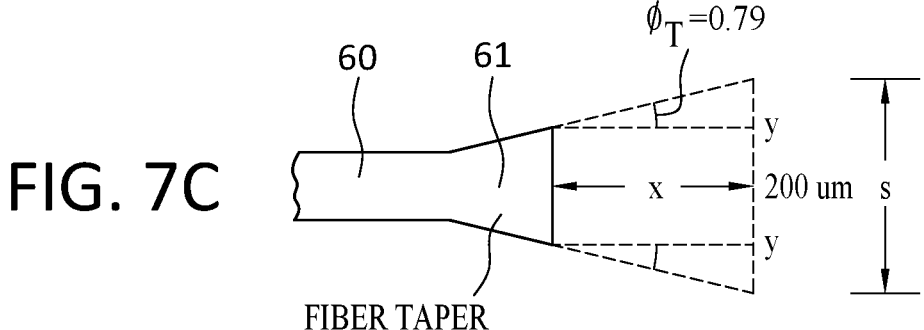

For example, as illustrated in FIGS. 7A-7C, the principles of the illustrated embodiments of the present invention may be applied to a fiber 60 having a core diameter $D_1$ of 25 μm, as shown in FIG. 7A. Fiber 60 has a numerical aperture (NA) of 0.11, and therefore the divergence angle φ, determined by the well-known formula NA=n sin φ, is arcsin (0.11), which equals 6.31°.

To construct the taper and achieve increased power density with a minimum taper angle, a cone-shaped piece of fiber 61 having a numerical aperture that is higher than a numerical aperture of the main fiber 60 may be fixed to the end of the main fiber, as shown in FIG. 7B. The dimensions of the cone-shaped piece 61 are determined by the desired divergence angle $\phi_T$ and the inner diameter of the standoff 62, i.e., the space available for the widened end of piece 61. In the illustrated arrangement, the exit side of piece 61 has a diameter $D_2$ of 200 μm, and therefore the numerical aperture $NA_T$ for piece 61 is $NA_T=(D_1/D_2)$ NA=0.014, and the divergence angle $\phi_T$ is reduced from 6.31° to 0.79°.

By adding the tapered piece 61, the setback (x) between the end of the fiber and the distal end of the standoff can be increased to, for example, 1000 μm, without a substantial loss in power density. As shown in FIG. 7C, the corresponding increase (2 y) in beam size (s) relative to the fiber endface diameter $d_2$ for setbacks of x=400 μm and x=1000 μm is only 11 μm and 28 μm, respectively.

Figure 7D:
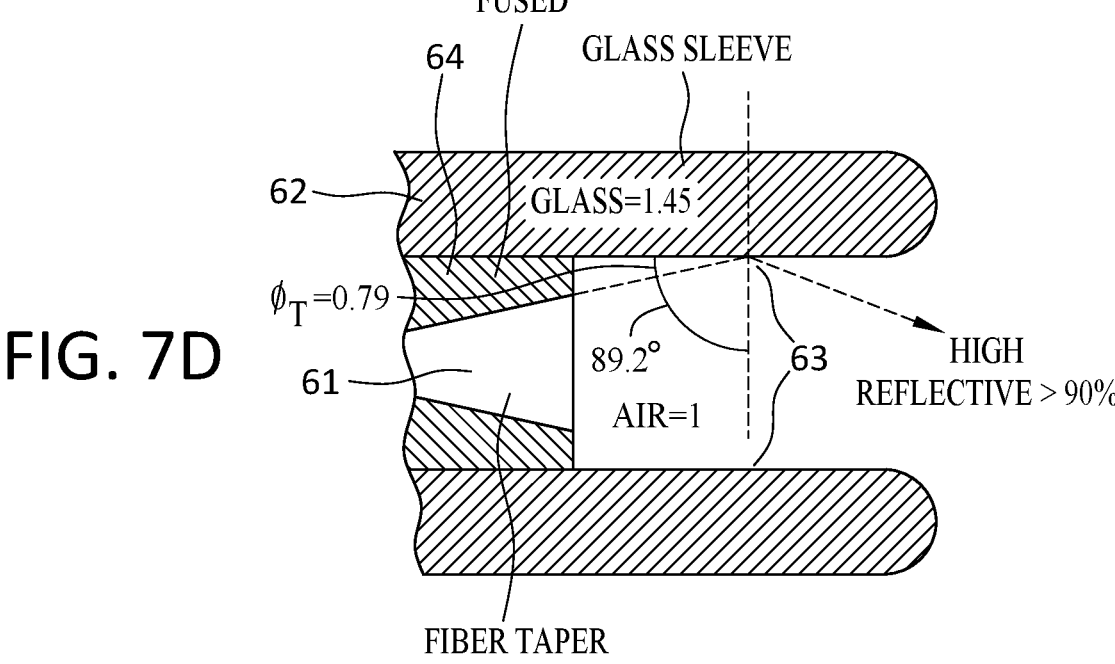

As illustrated in FIG. 7D, the standoff 62 of this embodiment (which may include apertures 14 shown in FIGS. 2-5 as well as any other features described above), may be made of glass with an index of, for example, 1.45, and be provided with a highly reflective (greater than 90%) inner surface 63 of the type described in the above-cited copending provisional U.S. Patent Application Ser. Nos. 63/324,676 and 63/247,427. In addition, the standoff 62 illustrated in FIG. 7D may be fused at location 64 to the interior of the standoff, as also disclosed in the copending provisional applications.

Finally, although preferred embodiments of the invention have been described in connection with the appended drawings, it will be appreciated by those skilled in the art that the description of the preferred embodiments is not intended to be limiting, and that modifications of the preferred embodiments may be made without departing from the scope of the invention, which should be limited solely by the appended claims. For example, while the fiber and metal, glass, or sapphire standoff sleeve illustrated herein are particularly adapted for use with Thulium Laser Fiber (TFL) lithotripsy systems, both the standoff 10 of the first preferred embodiment and the standoff sleeves 20 of the second and third embodiments may be used with lasers other than continuous wave Thulium lasers, including pulsed laser systems, and end-firing lasers for procedures other than laser lithotripsy. In addition, the materials of the standoff sleeve and any filler may be varied, as may the manner in which the standoff sleeve is fixed to the tapered section of the fiber. Still further, the dust particle buildup prevention method is not limited to use with standoff sleeves or members of the type described in detail herein, but my be rather may be used with any structure situated at the tip of the fiber that has a surface subject to dust accumulation. Moreover, the standoffs of the preferred embodiments, including but not limited to those that are open or extend along just one side of the fiber, may conveniently be used to mount a variety of different sensors or other devices for monitoring conditions at the treatment site, including by way of example and not limitation, radiation and/or proximity sensors for detecting the composition, presence or position of an object such as a stone.

What is claimed is:

1. A standoff arrangement for a laser lithotripsy fiber, comprising:
   an optical fiber having an end face through which laser energy is delivered during a lithotripsy procedure from a laser to a targeted stone at a distal end of the optical fiber; and
   a standoff fixed to the distal end of the optical fiber,
   wherein the standoff extends a predetermined distance beyond the end face of the fiber to prevent contact between the end face of the optical fiber and the targeted stone; and
   wherein the standoff extends from only one side of or only partially around a circumference of the optical fiber to prevent dust from being trapped within or accumulating on a surface of the standoff.

2. A standoff arrangement as claimed in claim 1, wherein the standoff is made of metal, silica glass or sapphire, or ceramic.

3. A standoff arrangement as claimed in claim 1, wherein the laser is a Thulium fiber laser.

4. A standoff arrangement as claimed in claim 1, wherein the standoff is fixed to a cladding of the optical fiber.

5. A standoff arrangement as claimed in claim 1, wherein a distal end of the optical fiber is outwardly tapered to reduce output beam divergence.

6. A standoff arrangement as claimed in claim 5, wherein a cone-shaped piece of fiber material having a numerical aperture that is higher than a numerical aperture of the optical fiber is fixed to the distal end of the optical fiber to provide the outward taper.

7. A standoff arrangement as claimed in claim 6, wherein a distal end of the cone-shaped piece is fused to the standoff.

8. A standoff arrangement as claimed in claim 1, wherein a sensor or detector is mounted on the standoff.

9. A standoff sleeve arrangement for a laser lithotripsy fiber, comprising:

an optical fiber having an end face through which laser energy is delivered during a lithotripsy procedure from a laser to a targeted stone at a distal end of the optical fiber; and a standoff sleeve fixed to the distal end of the optical fiber, wherein the standoff sleeve extends a predetermined distance beyond the end face of the fiber to prevent contact between the end face of the optical fiber and the targeted stone; and wherein the standoff sleeve includes at least one port configured to permit passage of dust particles from within the standoff sleeve to an exterior of the standoff sleeve during the lithotripsy procedure, thereby preventing accumulation of the dust particles within the standoff sleeve.

10. A standoff arrangement as claimed in claim 9, wherein the standoff is made of metal, silica glass or sapphire, or ceramic.

11. A standoff arrangement as claimed in claim 10, wherein the laser is a Thulium fiber laser.

12. A standoff sleeve arrangement as claimed in claim 9, wherein the standoff sleeve is fixed to a cladding of the optical fiber.

13. A standoff sleeve arrangement as claimed in claim 12, wherein the standoff sleeve is welded to the cladding of the optical fiber.

14. A standoff sleeve arrangement as claimed in claim 9, wherein a number of said ports is at least two.

15. A standoff sleeve arrangement as claimed in claim 9, further comprising a fluid source for introducing a fluid into a space between the end face of the optical fiber and a distal end of the standoff sleeve to thereby facilitate flushing of dust particles in the space.

16. A standoff sleeve arrangement as claimed in claim 15, wherein the fluid source is a source of liquid or gas.

17. A standoff sleeve arrangement as claimed in claim 9, wherein a distal end of the optical fiber is outwardly tapered to reduce output beam divergence.

18. A standoff sleeve arrangement as claimed in claim 9, wherein a cone-shaped piece of fiber material having a numerical aperture that is higher than a numerical aperture of the optical fiber is fixed to the distal end of the optical fiber to provide the outward taper.

19. A standoff sleeve arrangement as claimed in claim 18, wherein a distal end of the cone-shaped piece is fused to the standoff.

20. A standoff sleeve arrangement as claimed in claim 9, wherein a sensor or detector is mounted on the standoff.

* * * * *